United States Patent [19]

Berns

[11] Patent Number: 5,174,986
[45] Date of Patent: Dec. 29, 1992

[54] METHOD FOR DETERMINING ONCOGENIC POTENTIAL OF A CHEMICAL COMPOUND

[75] Inventor: Anton J. M. Berns, Spaarndam, Netherlands

[73] Assignee: GenPharm International, Inc., Mountain View, Calif.

[21] Appl. No.: 376,118

[22] Filed: Jul. 5, 1989

[51] Int. Cl.$^5$ .................... C12N 15/00; A61K 49/00
[52] U.S. Cl. .................................. 424/9; 800/21; 800/DIG. 1; 435/172.3; 435/317.1; 935/111
[58] Field of Search ............... 424/9; 800/2, DIG. 1; 435/172.3, 317.1; 935/111

[56] References Cited

U.S. PATENT DOCUMENTS 4,736,866  4/1988  Leder et al. .......................... 800/2

FOREIGN PATENT DOCUMENTS

WO89/05864  6/1989  PCT Int'l Appl. ..................... 800/2

OTHER PUBLICATIONS van Lohuizew et al., Cell 56: 673-682 (1989).
Selten et al., EMBO Journal 4(7): 1793-1798 (1988).
Selten et al., Cell 46: 603-611 (1986).
Berns et al., Proceedings of the Alfred Benzon Symposium 24, vol. 0(0): 211-220 (1987).

*Primary Examiner*—Elizabeth C. Weimar
*Assistant Examiner*—Jasemine C. Chambers
*Attorney, Agent, or Firm*—Flehr, Hohbach, Test, Albritton & Herbert

[57] ABSTRACT

Methods are provided for determining the oncogenic potential of chemical compounds which utilizes a transgenic mouse predisposed to T-cell lymphomas. The transgenic mouse expresses a pim-1 oncogene and as a consequence is predisposed to the spontaneous onset of T-cell lymphomas. The oncogenic potential of a chemical compound is determined by administering a known dose of the chemical compound of interest to a pim-1 transgenic mouse. Thereafter, the transgenic mouse is monitored to detect the onset of a T-cell lymphoma. The time of onset of the T-cell lymphoma and the dosage of the chemical compound are compared to either the onset of spontaneous T-cell lymphomas in the pim-1 transgenic mouse or to the onset of a T-cell lymphoma in a pim-1 transgenic mouse which has been exposed to a known quantity of a carcinogenic agent. This provides an indication of the oncogenic potential of the chemical compound.

3 Claims, 3 Drawing Sheets

FIG.-3

METHOD FOR DETERMINING ONCOGENIC POTENTIAL OF A CHEMICAL COMPOUND

FIELD OF THE INVENTION

This invention relates to methods for determining the oncogenic potential of chemical compounds utilizing an in vivo system comprising a transgenic mouse predisposed to the development T-cell lymphomas. More particularly, the invention relates to a method for determining oncogenic potential of chemical compounds utilizing a pim-1 transgenic mouse.

BACKGROUND OF THE INVENTION

Infection of mice with Moloney murine leukemia virus (MuLV) induces T cell lymphomas after an average latency period of 150 days. In these lymphomas, the MuLV DNA is frequently found integrated into the mouse chromosomal DNA in the vicinity of the pim-1 oncogene. Cuypers, H.T. et al. Cell 37, 141-150 (1984). In addition, thymomas (lymphocytic lymphomas of the thymus) of T-cell origin have been induced by N-methyl-N-nitrosourea in AKR mice which carry inherited copies of two types of leukemia virus (MuLV). Warren, W. et al. (1987) Carcinogenesis 8, 163-172.

It is an object of the invention herein to provide methods to determine the oncogenic potential of chemical compounds. Such methods are highly reproducible, simple and quick.

SUMMARY OF THE INVENTION

In accordance with the above objects, methods are provided for determining the oncogenic potential of chemical compounds. Such methods utilize a transgenic mouse predisposed to T-cell lymphomas. The transgenic mouse expresses a pim-1 oncogene and as a consequence is predisposed to the spontaneous onset of T-cell lymphomas. The oncogenic potential of a chemical compound is determined by administering a known dose of the chemical compound of interest to a pim-1 transgenic mouse. Thereafter, the transgenic mouse is monitored to detect the onset of a T-cell lymphoma. The time of onset of the T-cell lymphoma and the dosage of the chemical compound are compared to either the onset of spontaneous T-cell lymphomas in the pim-1 transgenic mouse or to the onset of a T-cell lymphoma in a pim-1 transgenic mouse which has been exposed to a known quantity of a carcinogenic agent. This provides an indication of the oncogenic potential of the chemical compound.

This method may be repeated with a number of chemical compounds to determine the relative oncogenic potential of such compounds.

BRIEF DESCRIPTION OF THE DRAWINGS

FIG. 3 shows the Expression of c-myc, N-myc, pim-1, and endogenous viruses by Northern blot analysis. Lanes A-E positive and negative controls. Lanes A, B and C represents RNA isolated from spontaneous lymphomas in E$\mu$-pim-1 transgenic mice. Lane E represents RNA isolated from a MuLV-induced lymphoma of a non-transgenic mouse. This lymphoma bares a proviral integration in the 3' untranslated region of the N-myc gene resulting in high expression of a slightly shorter transcript. Van Lohuizen, M. et al. Cell 56, 673-682 (1989). Lane D represent RNA from a MuLV-induced lymphoma of a E$\mu$-pim-1 transgenic mouse. In this lymphoma c-myc is highly overexpressed due to a proviral integration in c-myc. Lanes denoted with a "T" represent tumor RNA isolated from pim-1 mice. The numbers 2, 3, 4, 22, 23, 29, 32, 33, 36, 41, 42, 53 and 62 correspond to E$\mu$-pim-1 transgenic mice, the numbers 25, 28, 30, 34, 35, 37, 45, 46, 47, 49, 51, 54 and 55 to H$_2$K-pim-1 transgenic mouse but hardly expresses the transgene.

Figure 1:
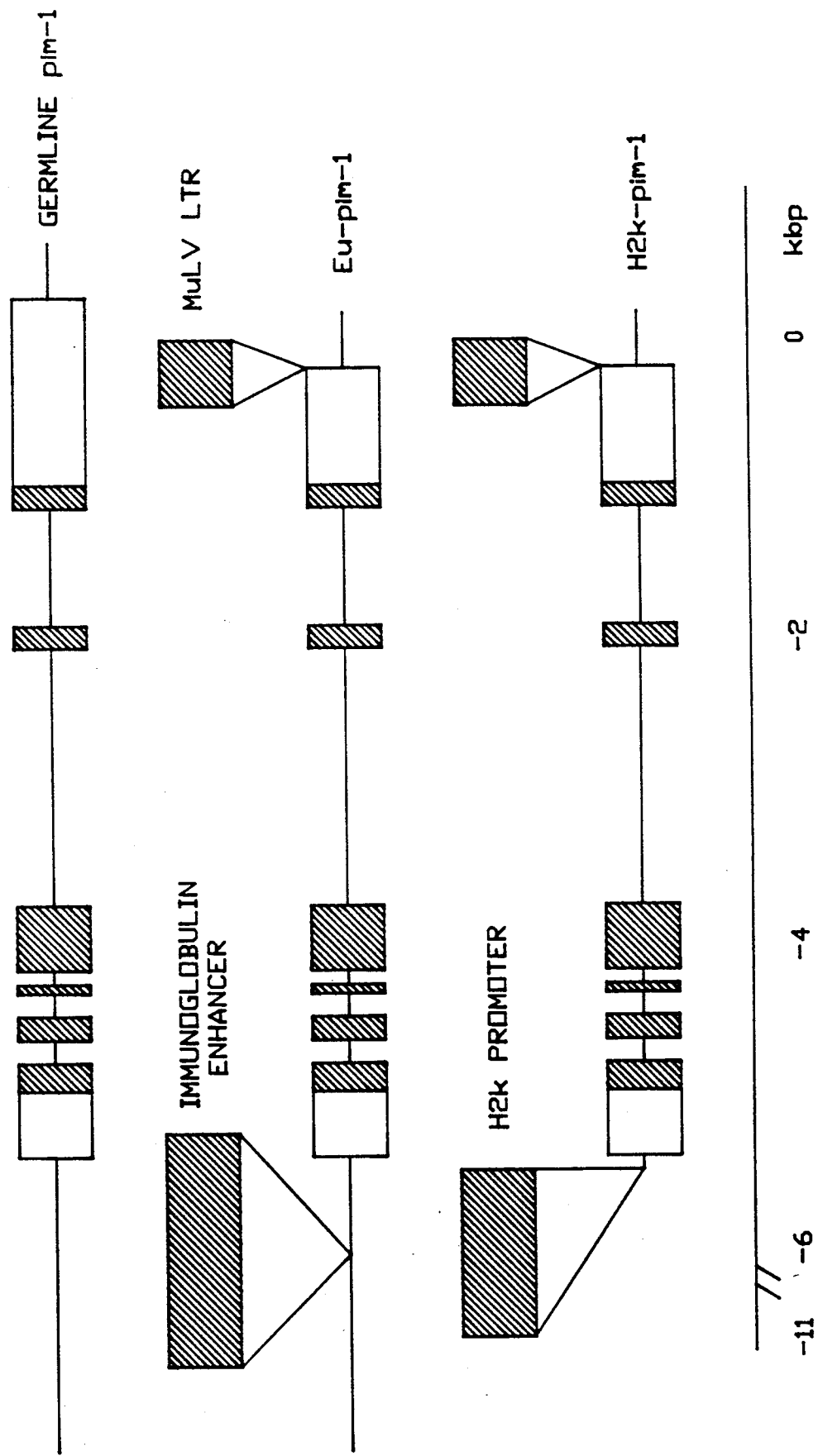
FIG. 1 depicts the construction of the transgene used to produce pim-1 transgenic mice. The upper panel shows the germline pim-1 genomic organization, in the middle panel the E$\mu$-pim-1 construct (Van Lohuizen, M. et al. (1989) Cell 56, 673-682) and the lower panel of the H2K-pim-1 construct.

Panel 1: Hybridization to a pim-1 specific probe; panel 2: hybridization to a 3'pim-1 probe that specifically detects the endogenous pim-1 transcript; panel 3: hybridization to a c-myc specific probe; panel 4: hybridization to a N-myc specific probe; panel 5: hybridization to a complete MuLV probe; panel 6: hybridization to an actin probe.

DETAILED DESCRIPTION

Transgenic mice expressing the pim-1 oncogene are predisposed to develop T-cell lymphomas but only to the extent that about 10% of the mice develop a lymphoma within 240 days. When these mice are infected with MuLV, lymphomas develop in all mice in only 50-60 days. Van Lohuizen et al. Cell 56, 673-682 (1989). In all these lymphomas MuLV DNA is integrated near either the c-myc or N-myc gene, suggesting that pim-1 and myc are synergistic in lymphomagenesis. Cuypers, H.T. et al. Cell 37, 141-150 (1984); Van Lohuizen et al. Cell 56, 673-682 (1989). To determine the susceptibility of pim-1 transgenic mice to chemical carcinogens, N-ethyl-N-nitrosourea (ENU) has been tested. With a single low dose of ENU, nearly all pim-1 transgenic mice, but only 15% of nontransgenic mice, develop T-cell lymphomas within 200 days. All ENU-induced lymphomas in both pim-1 transgenic and nontransgenic mice express high levels of c-myc mRNA. This supports the notion that pim-1 and c-myc are synergistic in lymphoma induction. Van Lohuizen et al. Cell 56, 673-682 (1989). Pim-1 transgenic mice can also be used to test the oncogenic potential of other chemical compounds.

As used herein, a "pim-1 transgenic mouse" is a transgenic mouse containing a pim-1 oncogene which is expressed at least in the T-cells of the transgenic animal. The pim-1 oncogene in mouse has been identified as a unique oncogene which does not show homology with other known or putative oncogenes based on the failure of the sequences encoding the pim-1 gene to hybridize with other oncogenic DNA sequences. Cuypers, H.T. et al. (1984) Cell 37, 141-150. In addition, the amino acid sequence of the pim-1 oncogene has been determined. Sulten, G. et al. (1986) Cell 46, 603-611. Other pim-1 genes from other murine species may be used. They may be identified as those genes which are capable of hybridizing with DNA sequences encoding the known mouse pim-1 oncogene as well as those which share primary sequence homology with the above mouse pim-1 oncogene.

Once a pim-1 gene is identified, enhancers which facilitate T-cell expression such as the Eµ enhancer sequence from the same or related animal species are positioned upstream from the pim-1 gene. Alternatively, T-cell specific promotor sequences such as the promoter from $H_2K$ may be operably linked to the pim-1 gene by replacing the normal pim-1 promotor sequence.

In a preferred embodiment long terminal repeat units (LTR'S) from leukemia viruses specific to murine species may be positioned down stream from the pim-1 gene to further enhance the T-cell expression of the pim-1 gene.

The above pim-1 gene containing enhancer and/or promoter and/or LTR sequences to enhance T-cell expression of the pim-1 gene may be excised from the cloning vector to form a transgene which is used to form transgenic mice by conventional methods. The transgenic animals so formed are predisposed to the development of T-cell lymphomas.

As used herein, a "carcinogenic agent" is defined as any agent that induces carcinoma. Such agents include viruses such as murine leukemia viruses (MuLV) and the like as well as chemical compounds such as N-methyl-N-nitrosourea, N-ethyl-N-nitrosourea, hexavalent chromium compounds, and other known carcinogenic compounds. Such known carcinogenic agents, in one aspect of the invention, may be used with the above transgenic mice to provide a time reference for the induction of T-cell lymphomas in the pim-1 transgenic mice. The time of T-cell lymphoma onset for chemical compounds can be determined and compared to this time reference as an indication of the oncogenic potential of that compound. In a preferred embodiment, a pim-1 transgenic mouse is used in conjunction with MuLV to determine the latency period after infection until the onset of T-cell lymphomas. In this particular system, the onset occurs approximately four weeks after inoculation with more than half of the infected population developing T-cell lymphomas by week 7 through 8 after inoculation. This latency period may be used as a first measure to compare the oncogenic potential of a chemical compound relative to MuLV. Thus, a specified dose of a chemical compound may induce T-cell lymphomas having a latency period which is greater than that of MuLV infection. The dose of such a compound can be increased or decreased so that the average latency period is the same as that for MuLV thereby providing a measure of the oncogenic potential of the chemical compound, i.e., $\times$ milligrams per kg of transgenic animal, has the same oncogenic potential as MuLV. Alternatively, a known carcinogenic chemical compound such as ENU may be used instead of MuLV. The latency period and dose required for the production of T-cell lymphomas may then be used to correlate the oncogenic potential of the chemical compound being tested.

Figure 2:
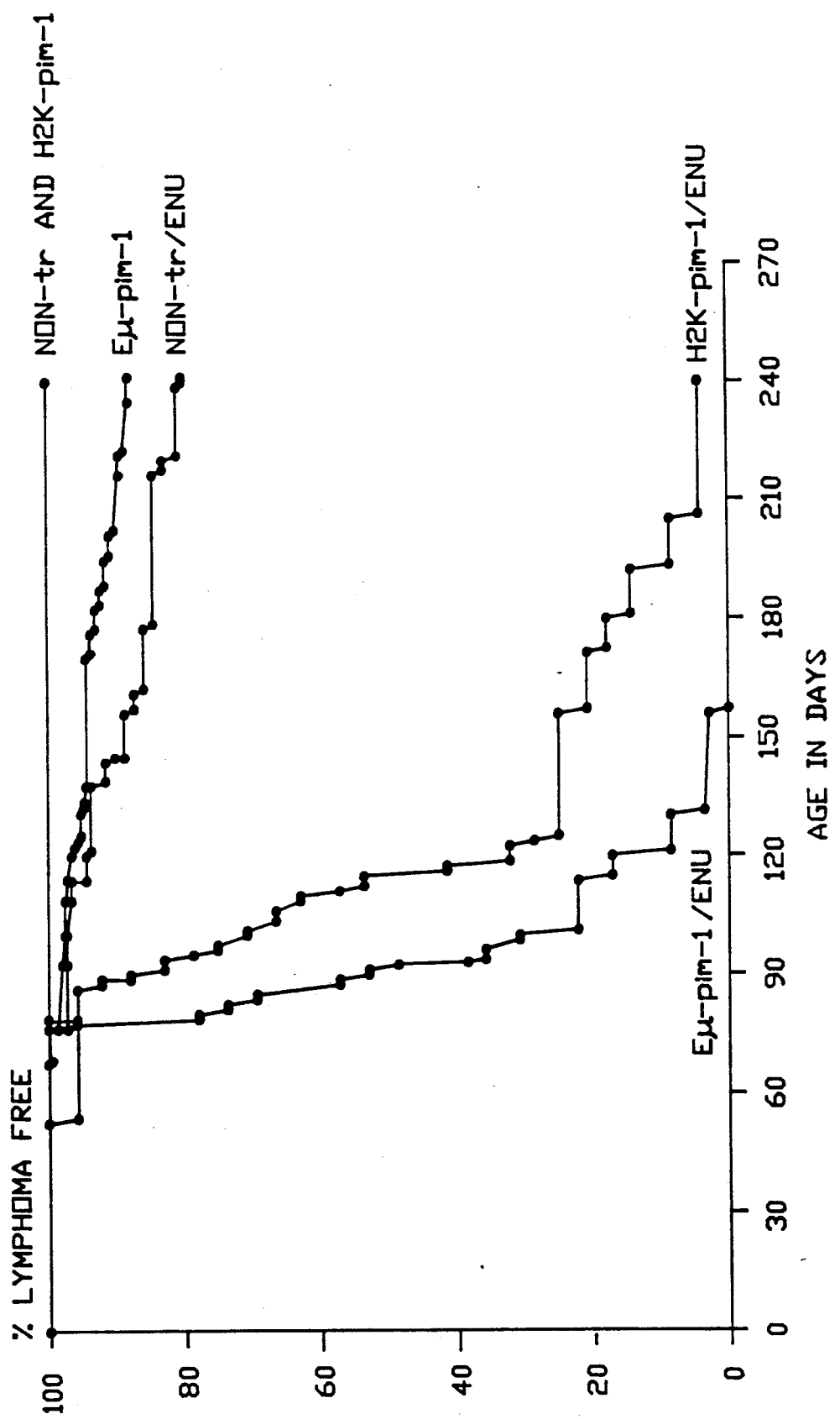
FIG. 2 depicts the N-ethyl-N-nitrosourea ("ENU")-induced lymphoma incidence in E$\mu$-pim-1, H$_2$K-pim-1 and control mice. Lymphoma-free survival of non-transgenic mice: without treatment (n=100), after ENU treatment (n=64), Lymphoma-free survival of E$\mu$-pim-1 transgenic mice: without treatment (n=200), after ENU treatment (n=23). Lymphoma-free survival of H$_2$K-pim-1 transgenic mice: without treatment (n=50), after ENU treatment (n=24).

Alternatively, the oncogenic potential of a chemical compound may be determined by the percentage of the transgenic mice developing T-cell lymphomas at a particular time after administration of a chemical compound. This time period is generally prior to the time of onset of spontaneous T-cell lymphomas in the transgenic mice. Such an analysis of oncogenic potential may be performed in conjunction with the induction of the T-cell lymphomas by known carcinogenic agents. Thus, as indicated in FIG. 2, approximately 80% of the Eµ-pim-1 transgenic mice develop T-cell lymphomas at approximately 100 to 110 days after birth (approximately 85 to 100 days after administration of ENU). The oncogenic potential of a particular chemical compound may be compared to ENU by determining the percentage of T-cell lymphomas present in Eµ-pim-1 transgenic mice during this same time period. Thus, a similar dose of a chemical compound which results in approximately 40% of such transgenic mice developing T-cell lymphomas at 85 to 100 days after administration has a lower oncogenic potential than ENU.

A third approach to determining oncogenic potential involves the measure of the rate of T-cell lymphoma development after onset of lymphomas. As shown in FIG. 2, after the onset of T-cell lymphomas in approximately 20% of the Eµ-pim-1 mouse population, only about ten days are required for the next 60% of the mouse population to develop T-cell lymphomas in response to EMU. A known dose of a different chemical compound may cause a rate of lymphoma development which is greater or less than that induced by ENU. Such a chemical compound would therefore have an oncogenic potential which is respectively greater than or less than the ENU.

In one aspect of the invention, a "chemical compound" does not include DNA or RNA but includes any chemical compound which does not cause the premature death of the transgenic animal. Thus, it is not practical to test the oncogenic potential of compounds such as cyanide, diphtheria toxin, etc. which cause the death of the transgenic animal prior to the onset of the T-cell lymphoma. Any other chemical compound, however, may be assayed for its oncogenic potential by the methods of the invention.

The method of administration of a chemical compound is not critical. However, the method of administration may provide useful information as to the oncogenic potential of a chemical compound in a particular environment. Thus, those compounds which may be used as food additives may be tested for oncogenic potential by administration in the transgenic animal's food whereas those chemical compounds intended for use in an aerosol spray may be tested by administration via inhalation. However, any form of administration may be utilized including injections, IP or IM, preferably IP.

MATERIALS AND METHODS

Two different pim-1 transgenic mouse lines were used in this study: Eµ-pim-1 and $H_2K$-pim-1 mice.

DNA Constructs

The constructs used to generate these mice are shown in FIG. 1. Both the Eµ-pim-1 and the $H_2K$-pim-1 transgene are expressed predominantly in lymphoid cells. Van Lohuizen et al. Cell 56, 673–682 (1989). The construction of the Eµ-pim-1 mouse is described in detail in Maarten van Lohizen et al (1989) Cell 56, 673–682. The $H_2K$-pim-1 construct was obtained by replacing the pim-1 promoter region entirely with the $H_2K$ promoter. The $H_2K$ promoter (Kimura et al. (1986) Cell 44, 261–272) was fused to the pim-1 sequence at the Pst I site at the boundary of the most 5' pim-1 exon using established procedures.

Generation of Transgenic Mice

The DNA fragments that were used for injection were released from the vectors with the appropriate restriction endonucleases and purified by agarose gel electrophoresis and electroelution. The final DNA concentration was adjusted to 4μg/ml. Fertilized mouse eggs were recovered in cumulus from the oviducts of superovulated (CBA/BrA×C57BL/LiA) F1 females that had mated with F1 males several hours earlier. The DNA fragments were injected into the most accessible pronucleus of each fertilized egg essentially as described. Hogan, B.L.M. et al. (Cold Spring Harbor Laboratory, Cold Spring Harbor, 1986) *Manipulation of the Mouse Embryo: a Laboratory Animal.* After overnight culturing two-cell-stage embryos were implanted into the oviducts of 1-day pseudopregnant F1 fosters and carried to term. Several weeks after birth of animals that had developed from microinjected eggs, total genomic DNA was prepared from tail biopsies as described. Hogan, B.L.M. et al. (Cold Spring Harbor Laboratory, Cold Spring Harbor, 1986) *Manipulation of the Mouse Embryo: a Laboratory Animal.* Transgenic founders were backcrossed with either (CBA/BrA×C57BL/LiA) F1 or with the C57BL/LiA parental strain.

Lymphoma Induction

Offspring of crosses between heterozygous transgenic (Eμ-pim-1 and $H_2K$-pim-1 ) and C57BL/LiA mice were injected IP at day 15 after birth with 60 mg/kg of body weight ENU, freshly dissolved in PBS acidified with acetic acid to pH 6. Mice were examined every other day for lymphoma development and sacrificed when moribund and the lymphomas collected for further analysis.

Northern Blot Analysis

For Northern blot analysis 25μg of total RNA, prepared by the LiCl-urea method was separated on 1% agarose formaldehyde gels (Selton, G. et al. (1984) *EMBO J.* 3, 3215-3222) and transferred to nitran as recommended by supplier. Probes used for RNA analysis: pim-1 probe A (Cuypers, H.T. et al. (1984) *Cell* 37, 141–150); the 3′pim-1 probe, inserted in M13, extends from genomic map coordinate 6619 (HindIII) to 6939 (BglII) (Selton, G. et al. (1984) *EMBO J.* 3215-3222). C-myc and N-myc probes (Cuypers, H.T. et al. (1984) *Cell* 37, 141–150; Van Lohuizen et al. (1989) *Cell* 56, 673–682), MuLV probe: a total MuLV provirus probe was used (Berns, A.J.M. et al. (1980) *J. Virol* 254–263), actin probe. Dodemont, H.J. et al. (1982) *EMBO J.* 167-171. These probes were $^{32}P$ labeled by nick translation (actin, pim-1 endogenous specific probe; hybridization conditions were as described (Cuypers, H.T. et al. (1984) *Cell* 37, 141–150) with addition of 1% SDS to all solutions, final wash was at 0.1×SSC, 60° C. except for the MuLV probe that was washed finally at 0.1×SSC, 42° C.

Detection of RAS Mutations

For the detection of ras mutations DNA sequences encoding the codons 12, 13 and 61 of both K-ras and N-ras were amplified by the Polymerase Chain Reaction (Saiki, R. et al. (1986) *Nature* 324, 163–166) performed essentially as described in Bos, J.L. et al. (1987) *Nature* 327, 293–207; and Verlaan-de Vries, M. et al. (1986) *Gene* 50, 313–320.

Results

Within 240 days, 10% of the Eμ-pim-1 mice developed spontaneous T-cell lymphomas whereas none of the $H_2K$-pim-1 or the control mice did. F1 offspring from crosses between non-transgenic mice and mice heterozygous for either Eμ-pim-1 or $H_2K$-pim-1 gene, were treated with a single ENU (N-ethyl-N-nitrosourea) dose of 60 mg/kg body weight at day 15 after birth. The lymphoma incidence of ENU-treated and non-treated transgenic and non-transgenic mice is shown in FIG. 2: Both the Eμ-pim-1 and $H_2K$-pim-1 mice show a strongly increased incidence of lymphomas with a reduced latency period after ENU treatment as compared to non-transgenic mice. The incidence of lymphomas found in non-transgenic mice is in accordance with other studies in which ENU and N-methyl-N-nitrosourea (MNU) were used to induce lymphomas in mice. Frei, J. et al. *Natl. Cancer Inst.* 64, 845–856 (1980).

Figure 3:
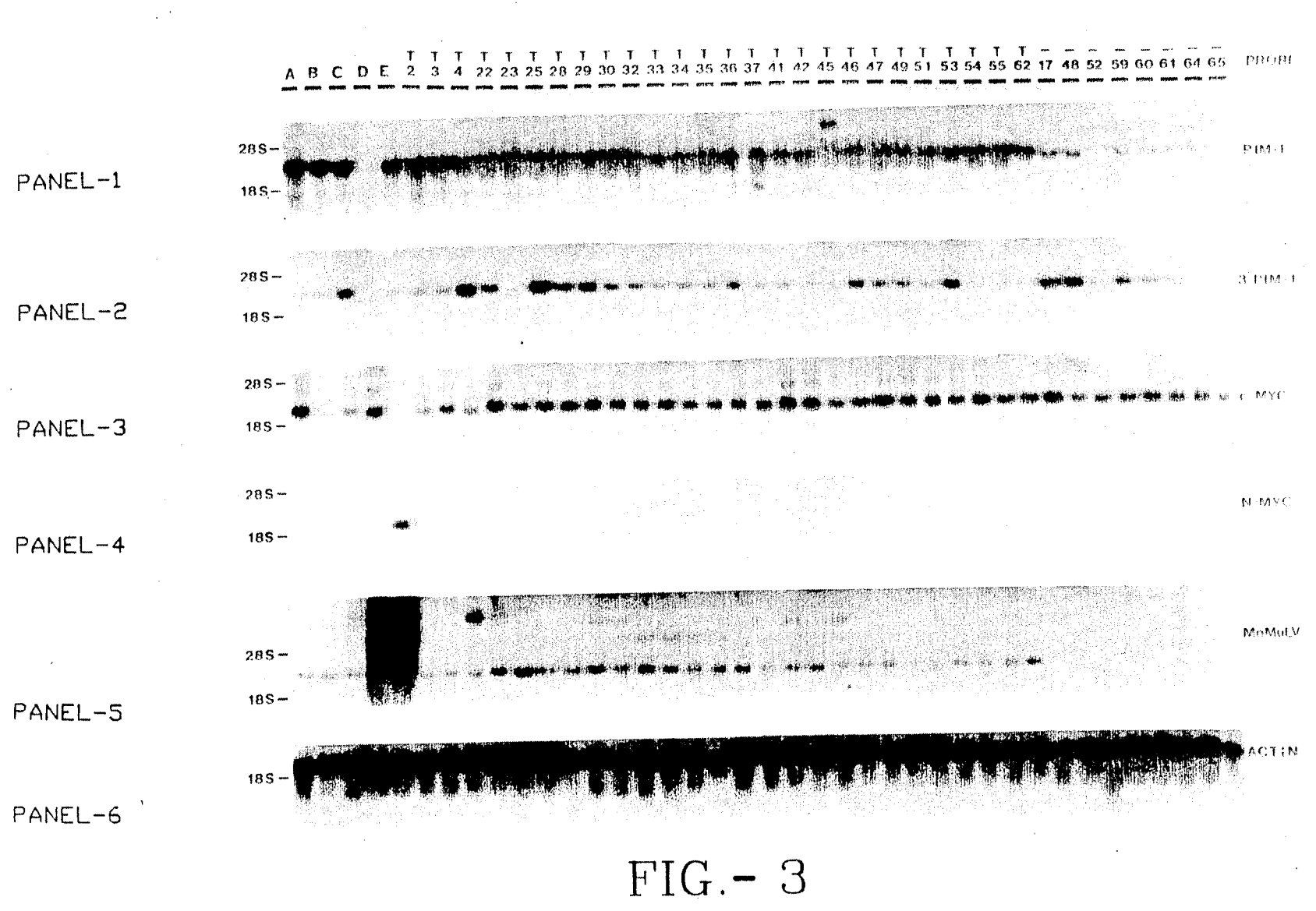

Since MuLV-induced lymphomagenesis in Eμ-pim-1 transgenic mice is mediated via the proviral activation of either the c-myc or N-myc gene, the expression levels of the c-myc and N-myc genes in lymphomas induced by ENU were determined. N-myc expression was not elevated in any of these lymphomas (FIG. 3, panel 4). In contrast, high levels of c-myc mRNA in lymphoma 2, 4, and 65 were still significantly elevated as compared to lane B, representing a lymphoma with a c-myc mRNA level similar to that normal spleen. The expression level of the majority of lymphomas was similar to that observed in lymphomas in which c-myc had been activated by proviral integration (FIG. 3, panel 3 compare control lanes D and E with the other lanes). The ENU-induced lymphomas were of T-cell origin as was evident from the clonal rearrangements of the T-cell receptor β chain gene (data not shown). FACS analyses using various T and B-cell specific cell surface markers (not shown) showed that the ENU-induced lymphomas were phenotypically indistinguishable from T-cell lymphomas occurring spontaneously in pim-1 transgenic mice or lymphomas induced by MuLV in non-transgenic mice. In a portion of these latter lymphomas no overexpression of c-myc or N-myc was found (e.g. tumors B and C in FIG. 3), indicating that a high c-myc expression is not an intrinsic property of these cells. Van Lohuizen et al. *Cell* 673-682 (1989). Therefore, it is unlikely that the high expression level of c-myc in ENU-induced lymphomas simply reflects the differentiation or growth state of the tumor cells. Rather, ENU is either a direct or indirect cause of the high c-myc mRNA levels. Since carcinogenic treatment can activate endogenous retroviruses, resulting in a viremia that, in turn, might activate proto-oncogenes by proviral insertion (Warren, W. et al. *Carcinooenesis* 8, 163–172 (1987)), we determined whether replication of endogenous retroviruses had been induced. Northern blots of lymphoma RNAs were hybridized to a probe containing an intact MuLV genome. This probe, which also hybridizes with the 2.8-kb pim-1 transcript in the transgenic strains due to the presence of an U3LTR within the transgene, showed additional hybridizing viral RNAs in some of the lymphomas (see FIG. 3, panel 5). However, the level of expression was extremely low (compare lanes D and E of MuLV-induced lymphoma RNA with lanes 4, 22, 29, 41, 45, 55, 17, 61 of ENU-induced lymphoma RNAs). In none of the lymphomas proviral insertions were found near the c-myc gene or the N-myc gene, as was the case in all MuLV-induced lymphomas in Eµ-pim-1 transgenic mice. Van Lohuizen et al. EMBO J. 8, 133-136 (1989). We conclude that the activation of endogenous retroviruses does not play a role in the ENU-induced lymphomagenesis in these pim-1 transgenic mice. As expected, high expression of the pim-1 transgenes were found in lymphomas of the Eµ-pim-1 and H2K-pim-1 transgenic mice. There is one exception, the lymphoma of the H2K-pim-1 transgenic mouse 64 hardly expresses the transgene (FIG. 3, panel 1). Remarkably, we observed a highly variable level of endogenous pim-1 expression in lymphomas of both pim-1 transgenic and non-transgenic mice (FIG. 3, panel 2). It is unlikely that selection for high endogenous pim-1 expression occurs in the presence of a highly expressed pim-1 transgene. Probably, the enhanced expression of the pim-1 germline allele is a secondary effect of the (in)activation by ENU of other genes.

Various studies have shown the involvement of the K-ras or N-ras, but not of H-ras in MNU-induced lymphomagenesis in mice. (Warren, W. et al. Carcinogenesis 8, 163-172 (1987); Diamond, L.E. et al. Mol. Cell. Biol. 8, 2233-2236 (1988). In these studies, up to 50% of the lymphomas were found to carry mutations in codon 12 in and in codon 12, 13 and 61 in N-ras. Screening mutations in codons 12, 13, or 61 of either K- or N-ras by oligonucleotide mismatch hybridization reevaluated that in six out of twelve lymphomas of non-transgenic mice a mutation in K-ras was detected, four in codon 12 and two in codon 61. In contrast, we found only three mutations, two in K-ras codon 12 and one in N-ras codon 61, in 22 lymphomas from Eµ-pim-1 mice and only one mutation, in N-ras codon 61, in 18 lymphomas of H2K-pim-1 mice (see Table 1). The lower incidence of mutations in K- or N-ras in lymphomas of pim-1 transgenic mice might be explained by a reduced selective advantage conferred by a mutation in ras in a cell already overexpressing the pim-1 transgene. Alternatively, one might argue that in both transgenic and non-transgenic mice the percentage of ras mutations with respect to number of animals treated with ENU is essentially the same (see Table 1). Further studies using varying doses of NEU will be required to gain more insight into the interaction between c-myc, pim-1, and ras in lymphogenesis.

TABLE 1

|  | non-transgenic | H2K-pim-1 | Eµ-pim-1 |
|---|---|---|---|
| Total number of mice | 65 | 24 | 23 |
| without lymphoma[a] | 52 | 1 | 0 |
| with lymphoma[a] | 13 | 23 | 23 |
| mice analyzed for mutation in ras | 12 | 18 | 22 |
| mice with mutation in ras | 6 | 1 | 3 |

Frequency of ras mutations in ENU-induced lymphomas in non-transgenic, H2K-pim-1, and Eµ-pim-1 transgenic mice.
[a]within a period of 240 days after ENU treatment.

Six out of ten lymphomas with a ras mutation lack the normal ras allele. Complete or partial loss of the normal allele has been reported for tumors bearing a mutated neu. Bargmann C. et al. Cell 45, 649-657 1986); H-ras, Quintanilla, M. et al. Nature 322, 78-80 (1986); and N-ras, Diamond, L.E. et al. Mol. Cell. Biol. 8, 2233-2236 (1986). The observed hemior homozygosity of the mutated allele suggests that a selective advantage is associated with the loss of the normal ras allele during lymphomagenesis.

In conclusion, the above results show that pim-1 transgenic mice represent a highly sensitive in vivo system for ENU-induced lymphomagenesis. The overexpression of c-myc in all ENU-induced lymphomas suggests that c-myc plays a pivotal role in the generation of these tumors. The low incidence of spontaneous tumors in pim-1 transgenic mice coupled to a nearly 100% lymphoma incidence after treatment with a single, relatively low dose of carcinogen indicates that pim1 transgenic mice are suitable to study the tumorigenic capacity of a diversity of chemical compounds.

The foregoing is presented by way of example only and should not be construed as a limitation to the scope of permissible claims.

Having described the preferred embodiments of the present invention, it will appear to those ordinarily skilled in the art that various modifications may be made to the disclosed embodiments, and that such modifications are intended to be within the scope of the present invention.

All references are expressly incorporated herein by reference.

What is claimed is:

1. A method for determining the oncogenic potential of a chemical compound comprising:
   (i) administering a known dose of said chemical compound to a first pim-1 transgenic mouse,
   (ii) detecting the onset of a T-cell lymphoma in said first pim-1 transgenic mouse, and
   (iii) comparing the dosage of said chemical compound and the time of onset of said T-cell lymphoma in said first pim-1 transgenic mouse to the time of onset of a spontaneous T-cell lymphoma in a second pim-1 transgenic mouse which has not been exposed to said chemical compound, as an indication of the oncogenic potential of said chemical compound.

2. A method for determining the oncogenic potential of a chemical compound comprising:
   (i) administering a known dose of said chemical compound to a first pim-1 transgenic mouse,
   (ii) detecting the onset of a T-cell lymphoma in said first pim-1 transgenic mouse, and
   (iii) comparing the dosage of said chemical compound and the time of onset of said T-cell lymphoma in said first pim-1 transgenic mouse to the time of onset of a T-cell lymphoma in a second pim-1 transgenic mouse which has been exposed to a known quantity of a known carcinogenic agent, as an indication of the oncogenic potential of said chemical compound.

3. The method of claim 2 wherein said known carcinogenic agent is murine leukemia virus or ENU.

* * * * *